United States Patent [19]

Lapidot

[11] Patent Number: 4,758,888
[45] Date of Patent: Jul. 19, 1988

[54] METHOD OF AND MEANS FOR INSPECTING WORKPIECES TRAVELING ALONG A PRODUCTION LINE

[75] Inventor: Zvi Lapidot, Rehovot, Israel

[73] Assignee: Orbot Systems, Ltd., Yavne, Israel

[21] Appl. No.: 15,070

[22] Filed: Feb. 17, 1987

[51] Int. Cl.⁴ .............................................. H04N 7/18
[52] U.S. Cl. ..................................... 358/106; 358/93; 358/101; 358/108
[58] Field of Search .................. 358/106, 101, 108, 93

[56] References Cited

U.S. PATENT DOCUMENTS

| | | | |
|---|---|---|---|
| 3,641,263 | 2/1972 | Rhoads | 358/93 |
| 4,209,802 | 6/1980 | Fogg et al. | 358/106 |
| 4,539,561 | 9/1985 | Wulff | 358/106 |
| 4,665,317 | 5/1987 | Ferriere | 358/106 |
| 4,698,664 | 10/1987 | Nichols | 358/185 |

Primary Examiner—Howard W. Britton
Attorney, Agent, or Firm—Sandler & Greenblum

[57] ABSTRACT

Inspection of workpieces traveling along a production line includes on-line inspection of the workpieces at an upstream inspection station to detect possible flaws without interrupting the progression of workpieces along the production line. Possible flaws in the inspected workpieces are imaged, and images of possible flaws are stored in a memory in a way that associates a stored image with the workpiece containing the possible flaw. Off-line, a stored image is retrieved from the memory before the workpiece with which the image is associated reaches a downstream sorting station. The retrieved image is displayed on a monitor for verifying, by visual inspection, whether the possible flaw in the workpiece with which the retrieved image is associated, is valid. Workpieces are diverted at the downstream sorting station in response to vertification of flaws.

15 Claims, 1 Drawing Sheet

METHOD OF AND MEANS FOR INSPECTING WORKPIECES TRAVELING ALONG A PRODUCTION LINE

TECHNICAL FIELD

This invention relates to a method of and means for inspecting workpieces traveling along a production line.

BACKGROUND ART

Continuous mass production of various products, ranging from processed food to steel slabs, hereinafter called workpieces, has required development of quality control systems that maximize the detection of actual flaws in the workpieces while minimizing disruption to the production line that produces and uses the workpieces. As a consequence, sophisticated flaw detection systems have been developed which use, for example, TV cameras that view the workpieces as they travel along the production line, and which allow an operator to divert those workpieces that the operator concludes have flaws. An example of this type of inspection is illustrated in U.S. Pat. No. 4,209,802 which discloses a system for inspecting baby food jars for foreign matter using a TV camera to produce an image of each jar as it travels down a production line at the rate of one jar a second. This type of flaw detection system is adequate only to the extent that a human operator is alert to the flaw being inspected.

When the number of possible flaws per workpiece is large, as for example, when the workpiece is a printed circuit board, real time, on-line inspection of each workpiece becomes very difficult. As a result, inspection systems have been developed which use computer assisted processing of TV images of a workpiece for the purpose of detecting flaws. A typical system is disclosed in U.S. Pat. No. 4,570,180 wherein a camera scans printed circuit boards as they are produced on as production line, and digital imaging processing techniques are used to detect possible flaws.

Because the flaw detection procedures are less than 100% accurate, the conventional procedure is to consider automatically detected flaws as being only "possible" flaws subject to manual verification. This requires a dedicated verification station to follow an automated inspection station. Thus, in the conventional approach, the automated inspection system tags those boards that contain possible flaws and diverts them to the verification station where human operators visually verify the system's findings. Using such manual inspection, those workpieces containing false alarms that arise from surface contamination, for example, or false defects that arise from irregularities within specifications, are separated from the diverted boards, and returned to the production line.

The conventional approach described above has two main disadvantages: creation of discontinuities in the production line, and unnecessary handling of workpieces. To verify a possible flaw in a workpiece requires the latter to be withdrawn from the production line and transferred to a manual inspection station. Even if it develops that all of the flaws were false alarms, and there was actually no need to withdraw the workpiece from the line, time, effort, and unnecessary handling of the workpiece results. Any unnecessary handling of workpieces increases the potential for additional flaws that may or may not be detected at a later stage of manufacture; and this adversely affects the reliability and quality of the end product.

It is therefore an object of the present invention to provide a new and improved method of and means for inspecting workpieces which overcomes the problems set forth above.

BRIEF DESCRIPTION OF THE INVENTION

In accordance with the present invention, inspecting workpieces traveling along a production line includes online inspection of the workpieces at an upstream inspection station to detect possible flaws without interrupting a progression of the workpieces along the production line. Possible flaws in the inspected workpieces are imaged, and images of possible flaws are stored in a memory in a way that associates a stored image with the workpiece containing the possible flaw. Off-line, a stored image is retrieved from the memory before the workpiece with which the image is associated reaches a downstream sorting station. The retrieved image is displayed on a monitor for verifying, by visual inspection, whether the possible flaw in the workpiece with which the retrieved image is associated, is valid. Workpieces are diverted at the downstream sorting station in response to verification of flaws.

When a complex workpiece is involved, such as a printed circuit board with many conductive traces, a given workpiece may contain many possible flaws. In such case, the location of each possible flaw in a workpiece, as well as the identification of the workpiece itself, will be stored. All, or a predetermined number of, possible flaws in any workpiece can be retrieved from storage and displayed, sequentially or simultaneous using split screen techniques, to an operator off-line at a remote location, as indicated above, or at a monitor at the automatic inspection station during the time that a succeeding workpiece is undergoing automatic inspection to the end that verification of the possible flaws can be made.

Using the method of the present invention, the flow of workpieces on the production line is uninterrupted because manual inspection of possible flaws in the workpieces is carried out off-line by inspecting stored images of the possible flaws rather than by directly inspecting the workpieces themselves. Moreover, no additional handling of the workpieces is involved because visual inspection is carried out off-line using stored images of possible flaws. Only if manual inspection of an image verifies that a possible flaw is an actual flaw is a workpiece containing an actual flaw diverted from the production line for rework or scrap.

DESCRIPTION OF THE DRAWINGS

An embodiment of the invention is shown in the accompanying drawing wherein.

DETAILED DESCRIPTION

Figure 1:
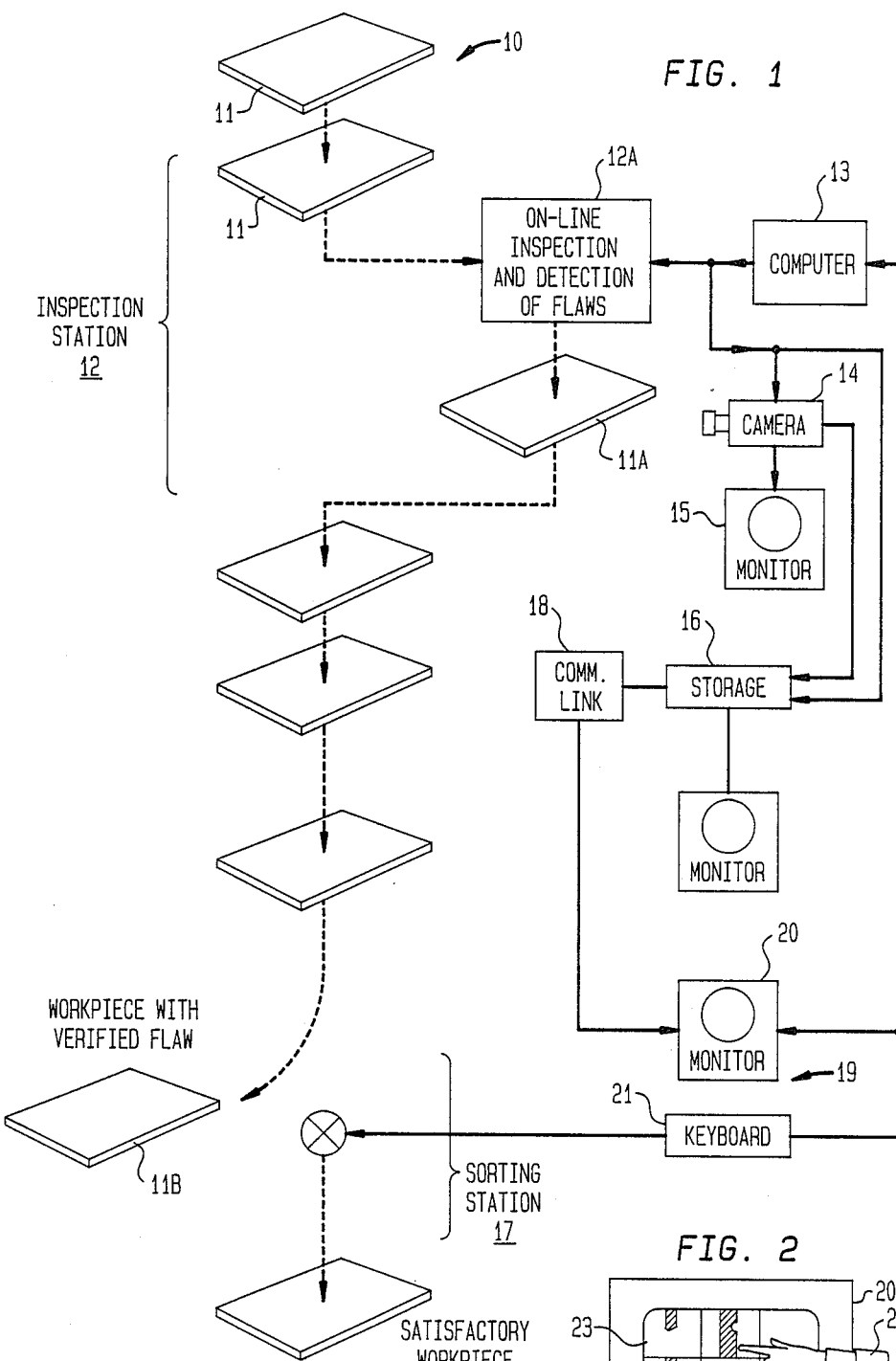
FIG. 1 is a schematic representation of a production line into which the present invention is incorporated.

Referring now to FIG. 1 of the drawing, reference numeral 10 designates a production line for mass producing workpieces 11, shown as printed circuit boards, but which are representative of individual items of any type produced in quantity by an industrial process, and which must be inspected for quality control purposes. Workpieces 11 pass through automatic inspection station 12 which includes apparatus 12A where a conventional inspection of the workpieces takes place using any of a number of conventional techniques for detecting possible flaws. Station 12A, its operation, and the procedures for detecting possible flaws are not a part of the present invention, and no further explanation of the operation of apparatus 12A is necessary to an understanding and use of the present invention except to note that the nature and location of possible flaws in a given workpiece are made known, by conventional procedures, to computer 13 supervising the operation of production line 10 and apparatus 12A.

Under command of computer 13, camera 14 images workpiece 11A, or a part thereof containing one or more possible flaws that apparatus 12A has detected. When the workpiece is a printed circuit board, for example, many different types of possible flaws located at various places on the workpiece. All of the possible flaws and their respective locations are ascertainable and can be cataloged in a conventional manner by the computer. The operation of apparatus 12A and of camera 14 by computer 13 are carried out in known ways without interrupting the progress of the workpieces travelling along production line 10.

Monitor 15, located at inspection station 12, displays the field seen by camera 14. This monitor, or an auxiliary monitor at the same location may be used, as explained below, to provide verification of possible flaws detected by apparatus 12A. In any event, images produced by camera 14 are stored in mass storage means 16 which may be a video tape recorder. Alternatively, the camera output may be digitized, and the data stored as a bit-map of possible flaws within the field of view of the camera. Storage of data in means 16 is accomplished in a way that associates a stored image of a possible flaw with the workpiece containing the possible flaw, as well as the location on the workpiece of the possible flaw. This may be achieved in conventional ways by serializing the workpieces and storing, with an image of a possible flaw, both the serial number of the workpiece containing the flaw, and the coordinates of the flaw on the workpiece.

The storage of data in storage means 16 takes place off-line as workpieces 11 continue to travel through apparatus 12A and along production line 10. Before the workpieces reach sorting station 17, downstream of inspection station 12, an off-line verification process is carried out to verify whether possible flaws are actual flaws. In one approach, data communication link 18 connects computer 13 and data storage means 16 to verification station 19, which may be remote from apparatus 12A, at which a human operator can selectively retrieve, for display on monitor 20, images stored in storage means 16. Keyboard 21 provides the operator with control over which image is to be displayed. Alternatively, link 18 can be used to display images stored in means 16 on monitor 15, or an auxiliary monitor located at the same station. The latter arrangement is advantageous when a significant amount of time is involved in the automated process by which possible flaws are identified and tagged by the operation of apparatus 12A. Thus, possible flaws in a given workpiece can be verified on monitor 15, or an auxiliary monitor at the same station, while the succeeding workpiece is undergoing automated inspection by apparatus 12A.

By a study of the images on monitor 20 of verification station 19, or monitor 15 at the inspection station, which images are one or more possible flaws associated with a particular workpiece that has not as yet reached sorting station 17, an operator can verify whether a possible flaw being displayed, is valid (i.e., whether the possible flaw is an actual flaw). In the event that the possible flaw being displayed on monitor 20 is an actual flaw, then the operator can so indicate by appropriate keyboard entry. Computer 13 in response to such appropriate keyboard entry responds by diverting workpiece 11B from the production line when the workpiece reaches sorting station 17. Otherwise, the workpiece is allowed to continue on the production line beyond the sorting station. By studying images of possible flaws off-line, rather than the workpieces containing the flaws, defective workpieces can be diverted to a repair or scrape process while the flow of workpieces remains uninterrupted. Moreover, actual handling of the workpieces is reduced thus minimizing the introduction of further possible flaws.

Figure 2:
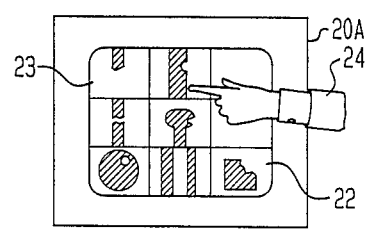
FIG. 2 is a schematic representation of a composite touch screen of a monitor on which a number of flaws in the same or different workpieces are displayed simultaneously.

In order to increase the speed of the verification process, all of the flaws associated with a given workpiece, or a number of workpieces, can be presented on monitor 15 or 20 simultaneously. This arrangement is suggested in FIG. 2 which shows monitor 20A having composite screen 22 that displays, in segments 23, a plurality of possible flaws in the same or different workpieces. By using what is termed a touchscreen, operator 24 may select those possible flaws that are actual flaws merely be physically touching that segment of the screen in which an image of the flaw is displayed. The touching of a segment of the screen by the operator is the input to the computer that signals the identification of an actual flaw. Instead of touching the screen, other known techniques could be used to identify for the computer those flaws that an operator ascertains are real. For example, a light pen could be used. The software may provide for text input by the operator on the screen of the monitor, or segments thereof, such that the text is stored in association with an image. The text may identify the type of defect displayed in an image, and may be inputted from a keyboard associated with the monitor, or by touching the screen successively an appropriate number of times, or by touching specific menus displayed on the screen with the images of possible flaws.

The advantages and improved results furnished by the method and apparatus of the present invention are apparent from the foregoing description of the preferred embodiment of the invention. Various changes and modifications may be made without departing from the spirit and scope of the invention as described in the claims that follow.

What is claimed is:

1. A method for inspecting individual workpieces progressing along a production line comprising the steps of:
   (a) on-line inspecting the workpieces at an upstream inspection station to detect possible flaws without interrupting a progression of the workpieces along said production line;
   (b) imaging possible flaws in inspected workpieces;
   (c) storing images of possible flaws in a memory in a way that associates a stored image with the workpiece containing the possible flaw;

(d) retrieving a stored image from the memory before the workpiece with which the image is associated reaches a downstream sorting station;
(e) displaying the retrieved image on a monitor for verifying, by visual inspection, whether the possible flaw in the workpiece with which the retrieved image is associated, is valid; and
(f) diverting workpieces at said downstream sorting station in response to verification of flaws.

2. A method according to claim 1 wherein possible flaws are imaged with a video camera to produce a video image, and the video image is stored with indicia indicative of the workpiece containing the possible flaw.

3. Apparatus for inspecting individual workpieces progressing along a production line, said apparatus comprising:
(a) an upstream inspection station for on-line inspection of workpieces as they travel along said production line and detection of possible flaws in the workpieces;
(b) imaging means associated with the inspection station responsive to detection of a possible flaw for imaging the latter;
(c) storage means for storing images of possible flaws in such a way that associates a stored image of a possible flaw with the workpiece containing the same;
(d) a retrieval system including means for retrieving from said storage means, images of possible flaws, and a monitor on which images retrieved from said storage means are displayed for verifying, by visual inspection, the validity of a displayed possible flaw in the workpiece with which the displayed image is associated; and
(e) a downstream sorting station for diverting workpieces in response to verification of flaws.

4. Apparatus according to claim 3 wherein said monitor is remotely located with respect to said inspection station.

5. Apparatus according to claim 3 wherein said monitor is located at said inspection station.

6. Apparatus according to either of claims 4 or 5 wherein a plurality of images of possible flaws are displayed simultaneously.

7. Apparatus according to claim 6 wherein said monitor is constructed and arranged to respond to physically touching an image on the monitor for signaling verification of an actual flaw.

8. Apparatus according to claim 6 wherein a keyboard is associated with the monitor, and verification of an actual flaw is indicated by keyboard input.

9. Apparatus according to claim 6 including means for signaling verification of an actual flaw.

10. Apparatus according to claim 6 including means for signaling verification of an actual flaw, and means for effecting operator input to an image on the monitor.

11. Apparatus for inspecting individual workpieces progressing along a production line, said apparatus comprising:
(a) an upstream inspection station for on-line inspection of workpieces as they travel along said production line and detection of possible flaws in the workpieces;
(b) imaging means associated with the inspection station responsive to the detection of a possible flaw for imaging the latter;
(c) storage means for storing images of possible flaws in a way that associates a stored image of a possible flaw with the workpiece containing the same;
(d) a retrieval system including means for retrieving from said storage means, images of possible flaws, and a monitor on which images retrieved from said storage means are displayed for verifying, by visual inspection, the validity of a displayed possible flaw in the workpiece with which the displayed image is associated;
(e) a downstream sorting station for diverting workpieces in response to verification of flaws;
(f) said monitor being remotely located with respect to said inspection station, said monitor being constructed and arranged such that a plurality of images of possible flaws are displayed simultaneously.

12. Apparatus according to claim 11 wherein said monitor is constructed and arranged to respond to physically touching an image on the monitor for signaling verification of an actual flaw.

13. Apparatus according to claim 11 wherein a keyboard is associated with the monitor, and verification of an actual flaw is indicated by keyboard input.

14. Apparatus according to claim 11 including means for signaling verification of an actual flaw.

15. Apparatus according to claim 11 including means for signaling verification of an actual flaw, and means for effecting operator input to an image on the monitor.

* * * * *